United States Patent
Felder et al.

(10) Patent No.: US 10,709,129 B2
(45) Date of Patent: Jul. 14, 2020

(54) SYNERGISTIC COMBINATION OF BIS-(3-AMINOPROPYL)DODECYLAMINE AND SORBIC ACID

(71) Applicant: DDP SPECIALTY ELECTRONIC MATERIALS US, INC., Wilmington, DE (US)

(72) Inventors: Patrick T. Felder, Horgen (CH); Emmanuelle Christine Yvon, Horgen (CH); Alessandro Vezzoli, Horgen (CH); Maciej Szymeczko, Horgen (CH)

(73) Assignee: DUPONT SPECIALTY PRODUCTS USA, LLC, Wilmington, DE (US)

( * ) Notice: Subject to any disclaimer, the term of this patent is extended or adjusted under 35 U.S.C. 154(b) by 0 days.

(21) Appl. No.: 16/468,577

(22) PCT Filed: Oct. 25, 2017

(86) PCT No.: PCT/US2017/058218
§ 371 (c)(1),
(2) Date: Jun. 11, 2019

(87) PCT Pub. No.: WO2018/118207
PCT Pub. Date: Jun. 28, 2018

(65) Prior Publication Data
US 2019/0350199 A1 Nov. 21, 2019

Related U.S. Application Data

(60) Provisional application No. 62/438,045, filed on Dec. 22, 2016.

(51) Int. Cl.
*A01N 33/04* (2006.01)
*A01N 37/06* (2006.01)

(52) U.S. Cl.
CPC ............ *A01N 33/04* (2013.01); *A01N 37/06* (2013.01)

(58) Field of Classification Search
CPC ................................ A01N 33/04; A01N 37/06
See application file for complete search history.

(56) References Cited

U.S. PATENT DOCUMENTS

| 5,393,789 A | 2/1995 | Eggensperger et al. |
| 2007/0078118 A1 | 4/2007 | Levy et al. |
| 2008/0234387 A1 | 9/2008 | Wachtler et al. |
| 2017/0051234 A1 | 2/2017 | Foster et al. |

FOREIGN PATENT DOCUMENTS

| EP | 0482328 A1 | 4/1992 |
| EP | 1332675 A2 | 6/2003 |

*Primary Examiner* — Gina C Justice

(57) ABSTRACT

A synergistic antimicrobial composition containing bis-(3-aminopropyl)dodecylamine and sorbic acid is provided. Also, a method of inhibiting the growth of or controlling the growth of microorganisms in an aqueous medium and an aqueous based product is further provided.

6 Claims, No Drawings

SYNERGISTIC COMBINATION OF BIS-(3-AMINOPROPYL)DODECYLAMINE AND SORBIC ACID

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. Additionally, synergy has been found to be an unpredictable phenomenon. Often like compounds display varying synergistic profiles when combined with a particular active. It may be that no synergy is evidenced or it may be that synergy exists but over a different synergistic range. Because of this observation, it is difficult, if not impossible to draw conclusions regarding the synergistic profile of one compound based upon the synergistic profile of a like compound. Thus more synergistic combinations and their synergistic ranges must be discovered.

One such example of synergy is found in U.S. Pat. App. Pub. No. 2007/0078118. This reference discloses synergistic combinations of N-methyl-1,2-benzisothiazolin-3-one (MBIT) with other biocides. There still exists a need for additional combinations of antimicrobial compounds having enhanced activity to provide effective control of microorganisms. The problem addressed by this invention is to provide such combinations of antimicrobial compounds.

In the present invention there is provided a synergistic antimicrobial composition comprising bis-(3-aminopropyl) dodecylamine (also known as BDA or diamine or triamine) (CAS registry number is 2372-82-9) and sorbic acid (also known as SA) (CAS registry number is 110-44-1). Sorbic acid also includes the acid and salt forms, for example, without limitation, potassium sorbate.

The invention further provides a method of inhibiting the growth of or controlling the growth of microorganisms in an aqueous medium, the method comprising the step of adding a synergistic antimicrobial composition comprising BDA and SA.

The following is a detailed description of the invention.

As used herein, the following terms have the designated definitions, unless the context clearly indicates otherwise.

The term "antimicrobial compound" refers to a compound capable of inhibiting the growth of or controlling the growth of microorganisms; antimicrobial compounds include bactericides, bacteriostats, fungicides, fungistats, algaecides and algistats, depending on the dose level applied, system conditions and the level of microbial control desired. Such term "antimicrobial compound" as used herein is synonymous with the term "biocide".

The term "microorganism" includes, for example, fungi (such as yeast and mold), bacteria and algae.

The following abbreviations are used throughout the specification: ppm=parts per million by weight (weight/weight), mL=milliliter, ATCC=American Type Culture Collection, DSMZ=Deutsche Sammlung von Mikroorganismen and Zellkulturen, and MIC=minimum inhibitory concentration.

Unless otherwise specified, temperatures are in degrees centigrade (° C.), and references to concentrations of antimicrobial compounds in the composition of this invention are described in parts per million (w/w) based on the total weight of active ingredients in the composition, i.e., the antimicrobial compounds themselves, exclusive of any amounts of solvents, carriers, dispersants, stabilizers or other materials which may be present.

When a ratio is the herein to be "X:1 or higher," it is meant that the ratio is Y:1, where Y is X or greater, and when a ratio is the herein to be "X:1 or lower," it is meant that the ratio is Z:1, where Z is X or less. The same logic follows for ratios that are "1:X or higher" and "1:X or lower". All range endpoints in this invention are inclusive and combinable.

The present invention is a composition that contains both BDA and SA. It has been surprisingly found that compositions that contain both BDA and SA are synergistically effective as biocides. In the present invention, the weight ratio of the BDA to SA is from 1:1 to 1:100 and alternatively from 1:10 to 1:100.

In some embodiments of the invention, the antimicrobial combination of this invention is useful for inhibiting the growth of or controlling the growth of microorganisms in an aqueous medium or aqueous-based product. Such aqueous-based products include but are not limited to cooling water, air washers, heat exchangers, boiler water, pulp and paper mill water, ballast water, wastewater, metalworking fluids, fluids used in oil and gas exploration and production, latex emulsions, paint, coatings, adhesives, inks, tape joint compounds, pigment, water-based slurries, home and personal care products, detergents, filtration systems, toilet bowl cleaners, textile processing chemicals, leather treatment chemicals and leather production systems, or a system used therewith. In one embodiment the antimicrobial composition is used as an in-can preservative.

Typically, the amount of the biocide combination of the present invention for inhibiting the growth of or controlling the growth microorganisms is from 1 ppm to 10,000 ppm active ingredient. In some embodiments of the invention, the active ingredients of the composition are present in an amount of at least 2 ppm, alternatively at least 20 ppm, alternatively at least 100 ppm, alternatively at least 150 ppm, alternatively at least 200 ppm. In some embodiments, the active ingredients of the composition are present in an amount of no more than 5,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are in a liquid composition containing the biocide combinations.

The present invention also encompasses a method for inhibiting the growth of or controlling the growth of microorganisms in the use areas described above, especially in in-can preservative applications, by incorporating the claimed biocide combination into the materials.

The composition of the present invention contains BDA and SA. It is contemplated that some embodiments may contain one or more additional antimicrobial compound. The following are examples of the present invention.

EXAMPLES

The synergism of the biocides combination of the present invention was determined using the Minimum Inhibitory (MIC) test method described by Kull, F. C., et. al in *Applied Microbiology* 9:538-541 (1961).

The formula to calculate the synergy index (SI) is $$SI = Qa/QA + Qb/QB$$

Where
QA=minimum inhibitory concentration in ppm of compound A acting alone
Qa=minimum inhibitory concentration in ppm of compound A in the mixture.
QB=minimum inhibitory concentration in ppm of compound B acting alone.
Qb=minimum inhibitory concentration in ppm of compound B in the mixture.

Synergism of two biocides is demonstrated when the SI has a value less than 1. The mixtures showed an additive effect if SI is equal to 1 and antagonistic if SI is greater than 1.

The Minimum Inhibitory Concentration Test (MIC) is designed to evaluate the lowest concentration of a biocide, biocide blend or biocide combination to prevent bacteria growing in a defined broth.

Minimum Inhibitory Concentration (MIC) Testing Protocol:
The MICs of the single biocides BDA and SA as well as of combinations of these two actives (all in TSB) in 3 different ratios (1:1; 1:10, 1:100) were estimated against each of the 2 microorganisms *Pseudomonas aeruginosa* (DSMZ#939) and *Candida albicans* (DSMZ#1386).

The synergy testing was carried out as follows:
1. The test was executed with a Hamilton MLStarPlus robot using automated turbidity reading with BioTek Synergy H4 plate reader.
2. Biocide systems were prepared in 2.2 ml deep well plates by transferring and diluting biocides from stock solutions to first rows of the plates. The concentrations of biocides in stock bottles were adjusted to be 20× more concentrated than the highest desired concentration.
3. Then 15 subsequent serial dilutions with dilution factor 1.3 were performed resulting in 16 different concentrations for each system.
4. In the next step serially diluted biocide systems were transferred to the media blocks containing 850 µl of TSB medium which was adjusted to pH 5. For each biocide system 100 µl was transferred to the media, resulting in 950 µl of final volume of media+biocides
5. After preparation and mixing of the described systems, 4 aliquots of 190 µl were prepared in 96-well microtiter plates.
6. Preparation of the microbe suspension:

Bacterial Culture:
*Pseudomonas aeruginosa* DSM #939 ATCC#15442
The culture was maintained as a glycerol stock at −80° C. in cryovials. A cryovial was thawed and then 100 µl spread on a TSA agar plate. After incubation for 1 day at 30° C. the bacteria were harvested with buffer at pH 7.3. A total viable count on TSA plate was carried out and bacterial suspension was diluted in buffer in order to deliver ~2×10$^7$ CFU/ml.

Yeast Culture:
*Candida albicans* DSM #1386 ATCC#10231
The cultures were maintained as glycerol stocks at −80° C. in cryovials, are thawed and then 100 µl spread on MEA (malt extract agar) petri dishes.
The yeast strain plates were incubated at 28° C. for 1-2 days then harvested with buffer pH 5.0.
Based on total viable count results, the inoculum was prepared.

7. Each test sample (190 µl) was inoculated with the 10 µl of microbe suspension to provide a level of ~1×10$^6$ CFU/ml of the bacteria species and ~1×10$^5$ CFU/ml of the yeast species.
8. The test samples were mixed and incubated at 30° C. for 2 days (48 hours) when tested against bacteria and 3 days (72 hours), respectively, when tested against yeast.
9. Growth of the micro-organisms leads to turbidity after incubation, clarity indicates no growth. Reading of the results was carried out by measuring absorbance at 600 nm for each sample at the beginning of the test ($t_{zero}$) and after incubation ($t_{endpoint}$). $t_{endpoint}$ was chosen at 48 hours for bacteria and 72 hours for yeast. The difference in absorbance between $t_{endpoint}$ and $t_{zero}$ was used to determine growth (Δ>0.2) or no growth (Δ≤0.2). The lowest concentration that showed no growth in the broth after incubation is taken as the MIC value.

The MICs of single biocide and combinations thereof as well as the synergy indices are presented in Tables 1, 2, and 3.

TABLE 1

MIC results for single biocides (in ppm):

| | Active ingredients [ppm] | |
|---|---|---|
| | BDA | SA |
| *Pseudomonas aeruginosa* DSM# 939 | 200 | 1226 |
| *Candida albicans* DSM# 1386 | ≥260$^a$ | 725 |

$^a$The MIC was above the highest tested concentration of the active.

TABLE 2

MIC results for combinations of two biocides (in ppm)

| | BDA/SA | | BDA/SA | | BDA/SA | |
|---|---|---|---|---|---|---|
| Active ingredients | 1 | 1 | 1 | 10 | 1 | 100 |
| *Pseudomonas aeruginosa* DSM# 939 | 70 | 70 | 24.5 | 245 | 7.3 | 725 |
| *Candida albicans* DSM# 1386 | 200 | 200 | 31.9 | 319 | 3.3 | 330 |

TABLE 3

Calculated synergy indices for the combinations in Table 2

| | Ratio BDA:SA | | |
|---|---|---|---|
| | 1:1 | 10:1 | 100:1 |
| *Pseudomonas aeruginosa* DSM# 939 | 0.4 | 0.3 | 0.6 |
| *Candida albicans* DSM# 1386 | ≤1.0$^b$ | ≤0.6$^b$ | ≤0.5$^b$ |

$^b$The Synergy Index is calculated based on the MIC value of BDA being >260 ppm, the highest concentration tested. The actual synergy index is less than or equal to the value calculated in the table.

The invention claimed is:
1. A synergistic antimicrobial composition comprising bis-(3-aminopropyl)dodecylamine and sorbic acid.
2. The synergistic antimicrobial composition of claim 1, wherein the weight ratio of the bis-(3-aminopropyl)dodecylamine to sorbic acid is from 1:1 to 1:100.

3. An aqueous-based product comprising the synergistic antimicrobial composition of claim 1.

4. An aqueous-based product comprising the synergistic antimicrobial composition of claim 2.

5. A method of inhibiting the growth of or controlling the growth of microorganisms in the aqueous-based product of claim 3.

6. The method of claim 5 wherein the aqueous-based product is selected form the group consisting of cooling water, air washers, heat exchangers, boiler water, pulp and paper mill water, ballast water, wastewater, metalworking fluids, fluids used in oil and gas exploration and production, latex emulsions, paint, coatings, adhesives, inks, tape joint compounds, pigment, water-based slurries, home and personal care products, detergents, filtration systems, toilet bowl cleaners, textile processing chemicals, leather treatment chemicals and leather production systems.

\* \* \* \* \*